United States Patent [19]

Ayer

[11] 4,353,372

[45] Oct. 12, 1982

[54] MEDICAL CABLE SET AND ELECTRODE THEREFOR

[75] Inventor: George E. Ayer, Naperville, Ill.

[73] Assignee: Bunker Ramo Corporation, Oak Brook, Ill.

[21] Appl. No.: 120,421

[22] Filed: Feb. 11, 1980

[51] Int. Cl.³ .............................................. A61B 5/04
[52] U.S. Cl. .................................... 128/640; 128/696; 174/117 FF; 174/117 PC; 339/255 R
[58] Field of Search ................................ 128/639-644, 128/670, 671, 696, 783-786, 798; 174/117 F, 117 FF, 117 PC; 339/74 R, 174, 255 R, 261

[56] References Cited

U.S. PATENT DOCUMENTS

| | | | |
|---|---|---|---|
| 2,592,788 | 4/1952 | Branson ................................ | 173/269 |
| 3,253,595 | 5/1966 | Murphy, Jr. et al. ................ | 128/785 |
| 3,323,514 | 6/1967 | Barrett, Jr. .......................... | 128/639 |
| 3,543,761 | 12/1970 | Bradley .............................. | 128/784 X |
| 3,547,104 | 12/1970 | Buffington .......................... | 128/640 X |
| 3,631,851 | 1/1972 | Hesen ................................. | 128/696 |
| 3,662,757 | 5/1972 | Blackett ............................. | 128/798 |
| 3,710,303 | 1/1973 | Gallager, Jr. ...................... | 339/74 R X |
| 3,916,877 | 11/1975 | Beckman ............................ | 128/670 |
| 4,051,842 | 10/1977 | Hazel et al. ....................... | 128/640 |
| 4,054,348 | 10/1977 | Stroupe et al. .................... | 339/91 R |
| 4,121,575 | 10/1978 | Mills et al. ........................ | 128/644 |
| 4,155,354 | 5/1979 | Rasmussen ........................ | 128/640 |

FOREIGN PATENT DOCUMENTS 1441622 7/1976 United Kingdom ................ 128/639

OTHER PUBLICATIONS

Leask et al., "A Multi-Pole Printed Circuit Electrode", Lancet, #7432, May 16, 1974, p. 1082.

Marriott et al., "Improved ECG ... Leads", *J. Electrocardiography*, 10(2) 1977, 119-122.

*Primary Examiner*—Lee S. Cohen
*Attorney, Agent, or Firm*—Nicholas A. Camasto; John R. Hoffman

[57] ABSTRACT

A pair of ECG cable sets are adhesively secured to disposable body electrodes, and also plug into a junction box which in turn is connected to an ECG machine. Each cable set is formed by printed circuit techniques. A pair of flat support sheets of insulating material are glued together. Signal leads formed of conductive ink are printed on the interior surface of one of the support sheets, and shielding layers also formed of conductive ink are printed on both exterior surfaces of the support sheets, thus forming a flat, flexible sandwich structure which resists entanglement. Entanglement is further minimized because the individual branch leads of each cable set merge into a common truck. The cable sets terminate in the printed circuit connectors which plug directly into the junction box, and the latter has clamping mechanisms to secure the connectors in place. A flexible housing surrounds the junction box terminal board, and permits the clamping mechanisms to be operated by squeezing the housing. A metal-free disposable body electrode is provided for connection to flat attachment pads located at the terminal ends of the cable set. Each electrode has an attachment ring surrounding a conductive sponge. An adhesive layer secures the attachment pad mechanically to the ring, and a conductive ink terminal centrally located on the attachment pad is pressed against the sponge for electrical communication therewith.

18 Claims, 16 Drawing Figures

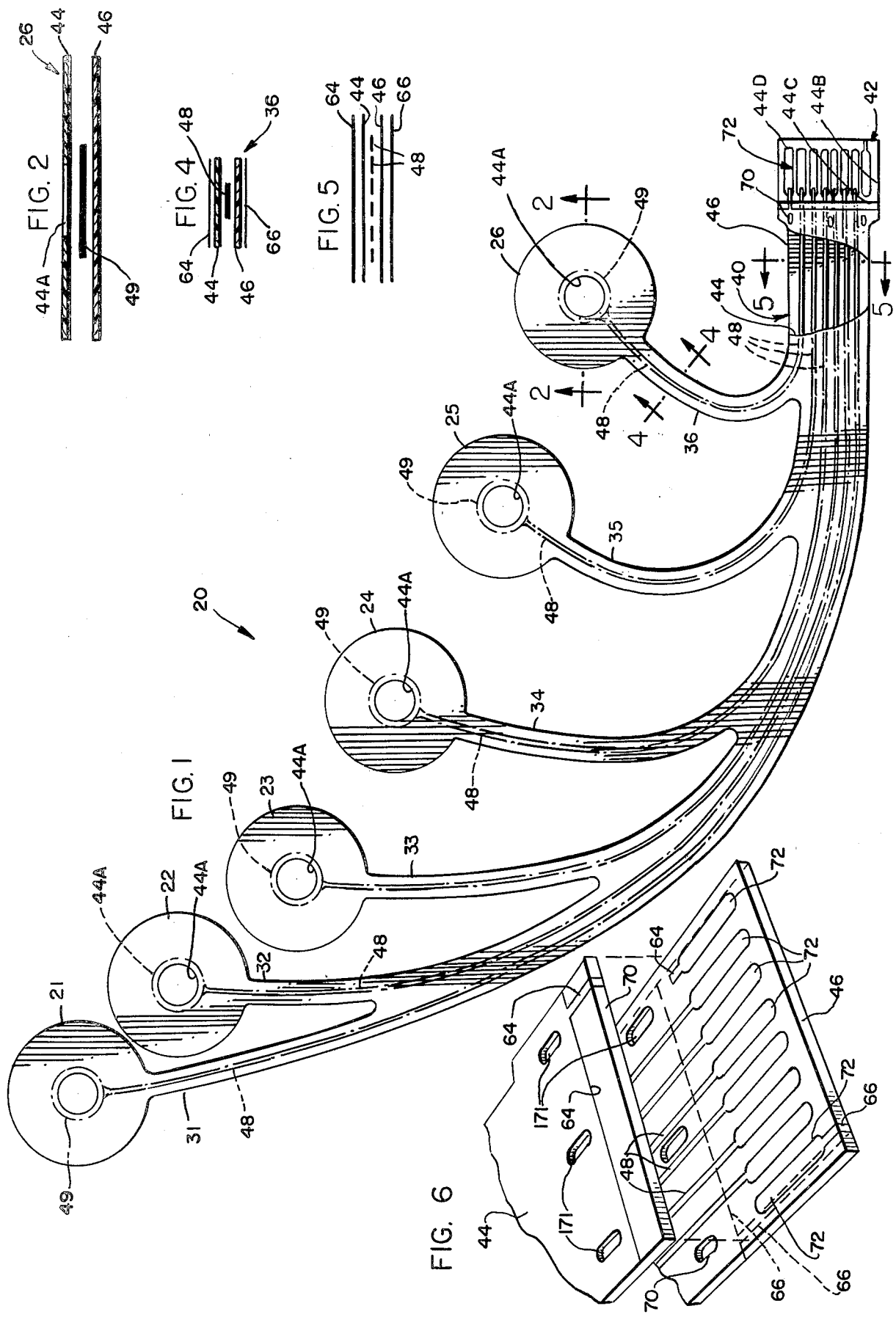

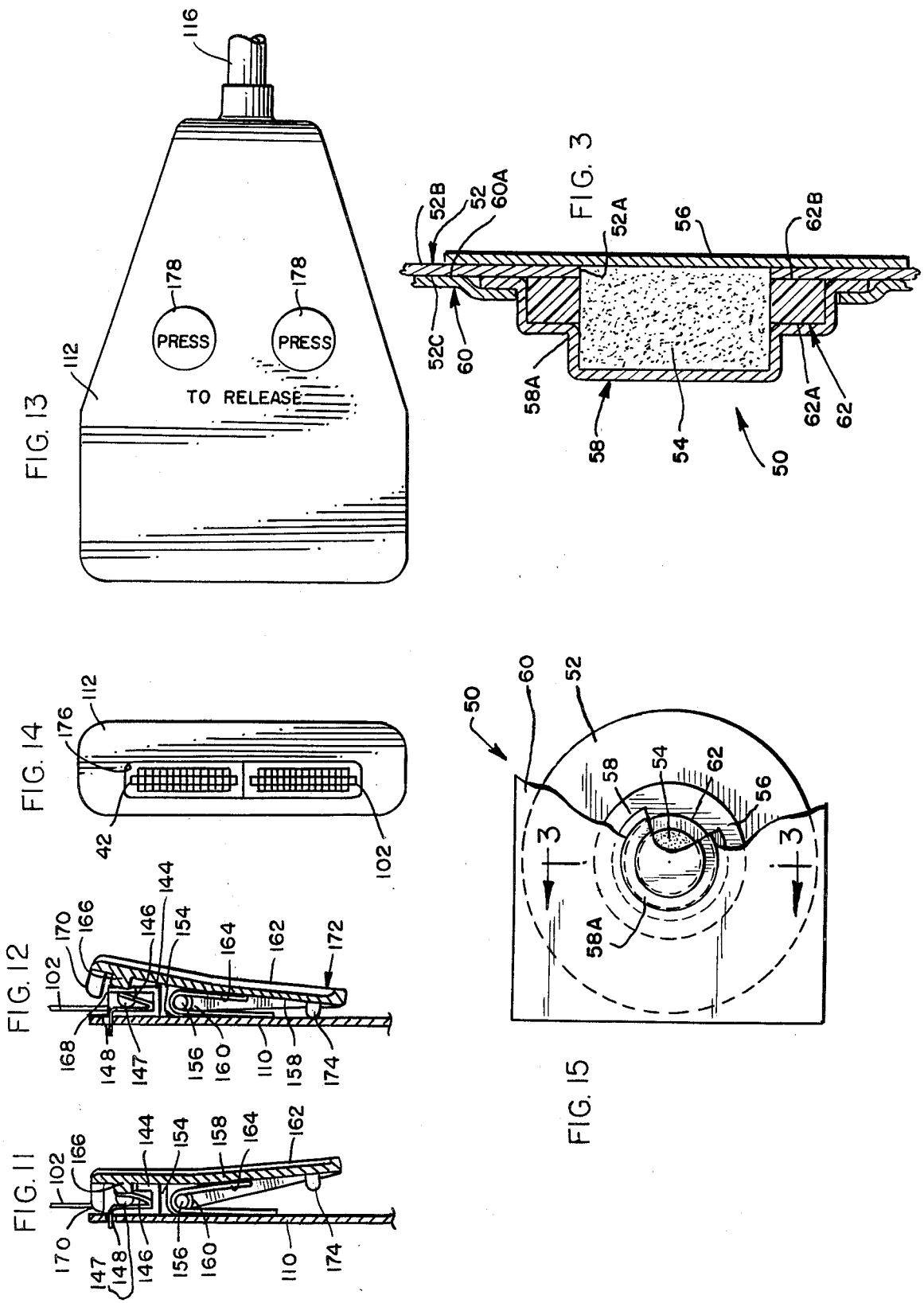

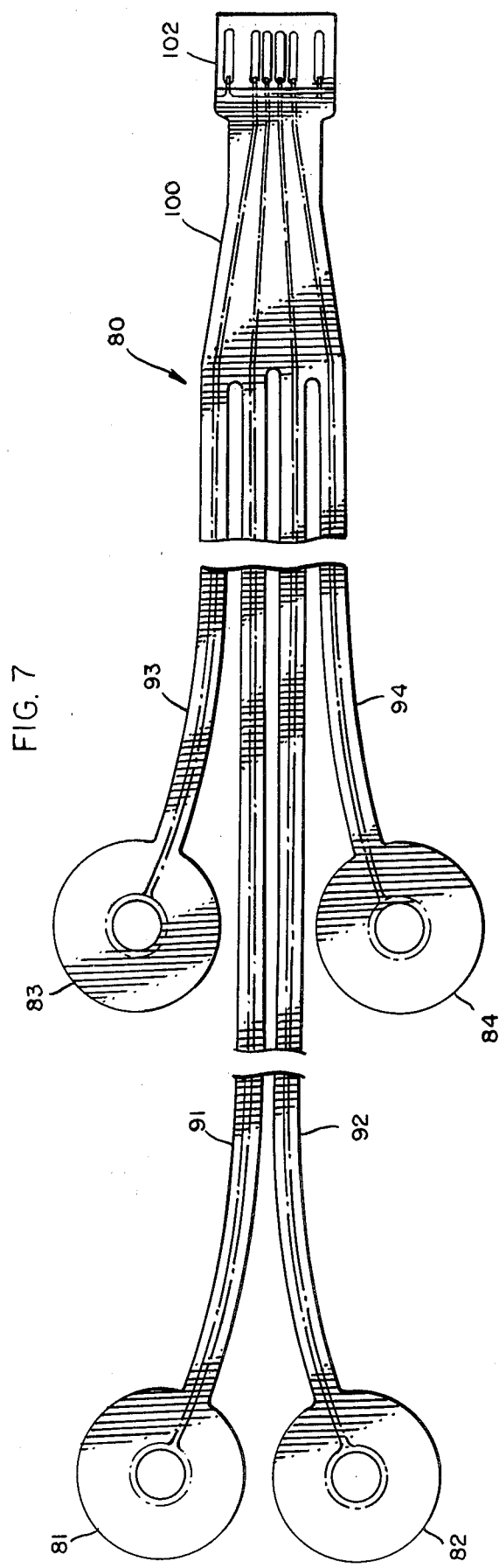

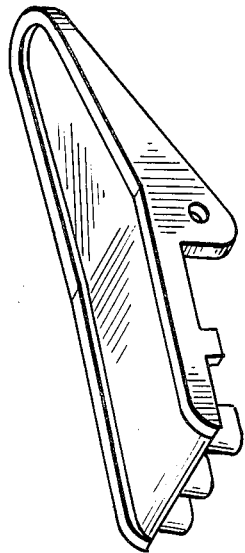
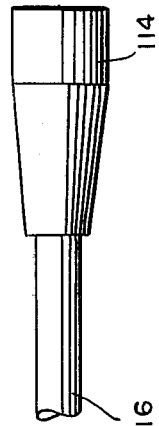

MEDICAL CABLE SET AND ELECTRODE THEREFOR

BACKGROUND OF THE INVENTION

This invention relates to disposable body electrodes, a cable set, and a junction box, all for use in making electrical body measurements.

Electrocardiogram (ECG) and electroencephalogram (EEG) measurements are important medical diagnostic procedures. Typically they involve the simultaneous application of disposable electrodes to several different body locations or groups of body locations, and the connection of these electrodes through suitable leads to ECG or EEG measuring equipment a short distance away.

In the past, disposable body electrodes used for such purposes have employed metal terminals for connection to the ECG leads. In many instances the metal used has been silver or some other expensive material. It is uneconomical for metals, and particularly precious metals, to be wasted in an electrode which is to be disposed of after a single use.

In taking an ECG it is usually necessary to apply electrodes to six different chest locations, as well as to four additional body locations, i.e. both arms and both legs; a total of ten locations and ten electrodes. In the past each of these ten electrodes has been connected to the ECG equipment by its own individual shielded lead. The use of ten discrete leads has proved somewhat inconvenient from two standpoints. First, the ECG technician is required to make ten separate plug connections to the ECG machine, which is time-consuming. Second, the ten individual leads have a tendency to become entangled with each other during use.

In other areas of electronic technology it is conventional for a plurality of leads to be grouped into a single unitary cable which terminates in a single connector. It is also conventional in other areas to make cables in a flat, flexible configuration, for example through the use of printed circuit manufacturing techniques. But so far as is known, no one has designed a single unitary cable of this kind specifically for use in ECG procedures and other types of body measurements.

This invention provides a completely metal-free disposable body electrode.

It also adapts the unitary cable and connector concept to the specific problem of taking medical measurements simultaneously from several body locations or groups of body locations. Such a cable resists entanglement, and such a connector permits connection of a plurality of leads in a single operation.

In addition this invention provides a specific flat, flexible printed circuit cable and connector structure and a compatible junction box assembly for use in making such measurements, both of which are inexpensive to manufacture and convenient to use. The junction box is also provided with clamping means which overcome any tendency of the printed circuit connector to slip out of the junction box.

SUMMARY OF THE INVENTION

In accordance with this invention, a unitary medical cable set is designed for electrical connection to a plurality of body locations. It comprises connector means having a plurality of contacts, and a plurality of electrical lead means each connected at one end to a respective one of the contacts. There are support means secured to the connector means, and supporting the lead means. The support means have a plurality of branches supporting respective ones of the lead means. At the ends of the branches and their respective lead means remote from the connector there are attachment means adapted to be secured mechanically and connected electrically to respective different body locations by means of disposable body electrodes.

There is also provided a metal-free disposable body electrode which comprises an attachment structure formed of non-metallic material, and having an aperture with electrically conductive means received therein. Respective non-metallic means are on axially opposite sides of the attachment structure for attaching one side thereof to the skin of a patient and the other side to electrical lead means, the latter including a conductor which extends at least partly across the mouth of the aperture. The electrically conductive means is thick enough to make simultaneous contact with both the skin and the conductor, for electrical communication therebetween.

These and other features of the invention are more fully set forth in the following detailed description of the accompanying drawings.

BRIEF DESCRIPTION OF THE DRAWINGS

FIG. 1 is a top plan view of an ECG cable set in accordance with this invention for use in making a group of simultaneous ECG measurements in the chest area of a patient.

FIG. 2 is a sectional view, taken along the lines 2—2 of FIG. 1, of a terminal end of one of the ECG leads of the cable set of FIG. 1.

FIG. 3 is a sectional view, taken along the lines 3—3 of FIG. 15, of a metal-free disposable body electrode in accordance with this invention, to which the terminal ends of FIGS. 1 and 2 are designed to be mechanically attached and electrically connected.

FIG. 4 is a sectional view, taken along the lines 4—4 of FIG. 1, of an individual ECG lead of the cable set of FIG. 1.

FIG. 5 is a sectional view, taken along the lines 5—5 of FIG. 1, of a common trunk region of the cable set thereof.

FIG. 6 is an exploded perspective view of the connector portion of the cable set of FIG. 1.

FIG. 7 is a top plan view of an ECG cable set in accordance with this invention for use in making a group of simultaneous measurements on the arms and legs of the same patient at the same time as the chest measurements referred to above.

FIG. 8 is a top plan view of the terminal board of a junction box into which the connectors of the ECG cables of FIGS. 1 and 7 are plugged.

FIG. 9 is a bottom plan view of the same terminal board.

FIG. 10 is a front elevational view of terminal strips mounted on the terminal board of FIGS. 8 and 9.

FIG. 11 is a sectional view, taken along the lines 11—11 of FIG. 8, of a portion of the same terminal board with the ECG cable connector of FIG. 7 plugged into it, and showing a rocket clamp in the closed position.

FIG. 12 is a side elevational view of a portion of the same terminal board, connector, and rocker clamp, the latter shown in the open position.

FIG. 13 is a top plan view of the entire junction box, including its external housing.

FIG. 14 is a front elevational view of the junction box.

FIG. 15 is a top plan view of the body electrode of FIG. 3, with parts broken away for clarity of illustration.

FIG. 16 is a perspective view of the rocker clamp of FIGS. 11 and 12, with parts broken away for clarity of illustration.

DETAILED DESCRIPTION OF THE PREFERRED EMBODIMENT

FIG. 1 depicts a unitary cable set 20 which combines in a single implement all the means necessary for connecting six different body electrodes to a common electrical junction box. The cable set 20 includes six different ECG electrode attachment pads 21 through 26, all for use in the chest area, and six individual branch electrical leads 31 through 36 which come from the respective attachment pads, and which all join to form a common trunk segment 40 terminating in a common connector plug 42.

This group of body electrode leads has been integrated into a single cable set, in contrast to certain prior art structures which employ six separate electrical leads having no fixed structural relationship to each other. That has several disadvantages worthy of comment. When several different leads are simultaneously connected to body electrodes all located in the same general region of the body, such as the chest, the arms, or the legs, these leads have a tendency to become entangled with each other and thus to impede the activities of the ECG technician. This can be merely a minor inconvenience during a routine annual medical check-up; or it could conceivably be a menace to life should it happen in the intensive care ward or during emergency situations in which an immediate ECG read-out is critical.

Also, the use of a unitary cable which terminates in a common connector, as in the present invention, permits six different electrical connections to be made in a single plug-in operation. This is at the least a convenience to the ECG technician, and may even be important when rapid set-up of the ECG is a medical necessity.

The detailed structure of electrode attachment pad 26, which is typical of all six pads 21–26, is revealed in FIG. 2. There it is seen that each attachment pad has a flat, flexible sandwich-like structure comprising two flat flexible outer layers 44 and 46 and a flat, flexible inner layer 48, 49 therebetween. Inner layer 49 is a circularly shaped pad made of an electrically conductive material. Leading away from conductive pad 49 is a thin line of material 48 (FIG. 1), which is also electrically conductive, and forms an electrical connection to pad 49. Outer layers 44 and 46 are formed of electrically insulating material, and are larger in width dimension than line 48 and pad 49, thus providing an insulating jacket therefor. Insulating outer layers 44 and 46 are preferably sheets of Mylar plastic, or a material having equivalent properties, while conductive inner layer 48, 49 is printed on Mylar sheet 46 with a conventional, silver-impregnated commercially available conductive ink. The two Mylar sheets 44 and 46 are glued together with a suitable adhesive, conductive inner layers 48 and 49 being located between them to form the sandwich structure. Alternatively, conductive inner layers 48 and 49 may be a sheet of flexible metal foil, with Mylar sheets 44 and 46 being glued to the foil sheet and to each other by a suitable adhesive. Whether formed of ink or foil, conductive inner layers 48 and 49 have little mechanical strength. Therefore, Mylar sheets 44 and 46, although relatively flexible, must not be limp; they must be sufficiently stiff to provide support for the conductive inner layer.

Attachment pads 21–26 are designed to cooperate with a novel form of disposable body electrode 50, seen in FIGS. 3 and 15, which has no metal parts whatsoever. An attachment ring 62 has a central aperture within which is axially inserted a porous, compressible open-cell plastic foam sponge 54. The sponge is impregnated with an electrolyte fluid, such as a conventional conductive gel, which serves as the electrical pathway of electrode 50. There is no other electrically conductive element, and no metal terminal or other metallic element, in the electrode.

One side 62A of ring 62 is coated with an adhesive to maintain electrode 50 in skin contact. Until the electrode is to be used, sponge 54 and the adhesive coating on surface 62A are protected by a plastic cap 58. Prior to use, this cap is pulled off, at which time the plastic material thereof releases easily from the adhesive film on surface 62A.

Attachment ring 62 also has an adhesive layer on the opposite surface 62B, which secures it to a base sheet 52. An adhesive layer on the outer surface 52B of the base sheet serves to secure one of the attachment pads 21–26 to electrode 50 without the use of any snap fastener or other metal terminal structure. The base sheet has a central aperture 52A through which sponge 54 is accessible to the attachment pad.

Ring 62 and sheet 52 are both formed of closed-cell plastic foam material or some other non-porous material which does not absorb the gel electrolyte from sponge 54. In order to protect the adhesive layer on ring surface 62A from the gel electrolyte, protective cap 58 has an annular indentation 58A which covers the entire ring surface 62A. A cover sheet 56 similarly protects the adhesive layer of base sheet surface 52B from the electrolyte.

A cover sheet 60 formed with a circular central opening to receive 58 traps the annular peripheral edge of the cap, there is an adhesive layer on sheet 52 surface 52C which sticks to surface 60A of base sheet 60. Both cover sheets 56 and 60 are preferably formed of paper, and must be peeled away prior to use of electrode 50. For this reason sheets 56 and 60 are coated with conventional release films in those areas which confront the respective adhesive coatings of base sheet 52. When sheet 56 is peeled away, adhesive-coated surface 52B may be secured to one of the attachment pads 21–26 and electrical contact may be made with the conductive gel within sponge 54. Removal of sheet 60 permits the other side of the electrically conductive sponge and of attachment ring 62 and 52 to contact the skin of the patient.

Referring again to attachment pads 21–26 of FIG. 2, an annularly shaped region on the outer surface of support sheet 44, i.e. the region which surrounds conductive pad 49, comes into contact with adhesive-coated surface 52B of base sheet 52, and adheres thereto for mechanical attachment of pad 21–26 to electrode 50. Support sheet 44 is formed with apertures 44A which permit inner conductive pads 49 to make electrical contact with conductive sponges 54 through apertures 52A, and thus to connect electrically to electrode 50. Note that this connection is achieved without the use of any snap fasteners or other metal parts on the disposable portion of the apparatus, i.e. electrode 50. Silver coating 49 is confined to attachment pads 21-26, which are reuseable.

Surface 62A of ring 62 and 52C of 52 is secured adhesevely to the skin of the patient. Conductive sponge 54 is substantially thicker than attachment ring 62, so that sponge 54 is then compressed to the thickness of attachment ring 62 between the patient's body and attachment pad 21-26. Such compression produces superior electrical contact on both sides of sponge 54.

The flat, flexible sandwich design described in connection with attachment pads 21-26 is carried through to branch leads 31-36, common trunk 40, and connector 42 of cable 20. In FIG. 4, for example, is shown a sectional view of lead 36, which is typical of all six leads 31-36. Here again there are the same support sheets 44 and 46 with conductive ink layer 48 between them. In addition, in the area of leads 31-36, the outer surfaces of support sheets 44 and 46 are covered by layers 64 and 66 respectively of conductive material for electrostatic shielding purposes. Preferably these shielding layers are formed by a conventional conductive ink printed (for example in a cross-hatch or screen pattern) directly on the outer surfaces of the support sheets. Alternatively, sheets of flexible metal foil may be glued to these surfaces. In either case shielding layers 64 and 66 have little mechanical strength, and are supported by the somewhat stiffer Mylar sheets 44 and 46.

Insulating coatings are preferably applied over the outside surfaces of shielding layers 64 and 66. Any flexible insulating material which is compatible with Mylar sheets 44 and 46 will do. One alternative is a coating of polyvinyl chloride which is sprayed over layers 64 and 66, and which then dries in place.

The Mylar support sheets are arranged to provide a complete insulating cover for inner conductive layers 48. Over the area of each individual branch lead 31-36, support sheets 44 and 46 are larger in the width dimension than the associated layer 48 (see FIG. 4).

In the area of common trunk 40 (see FIGS. 1 and 5), the individual lead branches of support sheets 44 and 46 merge. Individual inner conductive strips 48 of all six leads 31-36 converge but remain spaced apart from each other for mutual electrical isolation. In this region the width of support sheets 44 and 46 is great enough to encompass all of the conductive strips and the spaces between them, and also to provide a margin on the outer sides of the outermost ones of the conductive strips.

Exterior shielding layers 64 and 66 preferably extend over the entire width and length of support sheets 44 and 46 in the area of common trunk 40 (see FIG. 5) as well as in the area of branch leads 31-36 (see FIG. 4). The thickness of the insulating support sheets also serves to electrically isolate the conductive strips from the conductive shielding layers.

In sum, the ECG cable set 20 comprises a unique flat, flexible sandwich structure comprising sheets of semiflexible insulating material interleaved with flexible conductive ink layers which are mechanically supported on, and maintained in electrical isolation by, the insulating material.

This flat, flexible printed circuit design approach is carried through also to connector plug 42 at the end of trunk 40. Support sheet 46 and exterior conductors 64 and 66 all terminate at an edge 70. But the other support sheet 44 extends some distance beyond edge 70, this sheet extension being designated 44B. Most of the inner surface of support sheet 44 is hidden behind the support sheet 46, but at extension 44B a portion 44C of that inner surface is exposed, and bears eight printed circuit contact strips 72. The second through seventh contacts are for connection to the six chest electrodes respectively, while the first and eighth contacts are for connection to shielding layers 64 and 66 respectively. Contacts 72 are also formed of conductive ink, but preferably the ink in this case is impregnated with gold instead of silver, for the sake of electrochemical compatibility with the mating contacts of a junction box (to be described below).

As seen in FIGS. 1 and 6, each contact 72 extends from front edge 44D of extension 44B longitudinally rearwardly across exposed surface 44C to a location near edge 70. Thus contacts 72 are suitable for longitudinal insertion of plug connector 42 into an appropriate receptacle or female connector socket. Each interior conductor 48 extends some distance beyond edge 70 and across exposed surface 44C in order to establish electrical communication with a respective one of contacts 72, while a portion of exterior conductor 66 also extends forward beyond edge 70 and across exposed surface 44C to establish electrical communication with one of the contacts 72. As seen in FIG. 6, a portion of exterior conductor 64 extends forward across the outside surface of sheet 44, wraps around front edge 70, and extends across surface 44C to establish electrical communication with its particular contact 72. Alternatively, exterior shielding layer 64 on the outer face of sheet 44 may be brought through a hole formed in extension 44B, or it may be wrapped around a side edge of extension 44B, to establish electrical communication with a contact 72 on exposed surface 44C.

The same flat, flexible sandwich concept is employed in the design of another cable 80 (FIG. 7) which is used to make electrical measurements on the arms and legs of the patient at the same time as the chest measurements are in progress. Cable 80 includes two leg electrode attachment pads 81 and 82 and two arm electrode attachment pads 83 and 84 connected by respective individual branch leads 91 through 94, which merge into a common trunk 100, which in turn terminates in a connector 102. The structure of attachment pads 81-84 is identical to that of attachment pads 21-26 described above; the structure of the branch leads 91-94 is identical to that of branch leads 31-36 described above, except for lead length; the structure of common trunk 100 is identical to that of common trunk 40 described above, except that here there are four instead of six interior conductors; and the structure of connector 102 is identical to that of connector 42 described above, except that here there are only six contacts because there are only four signal leads to be connected (plus two electrostatic shields).

The use of the cable set concept, especially in conjunction with the flat sandwich design, not only reduces the likelihood of entanglement between any individual leads 91-94 of cable 80, but also reduces the likelihood of entanglement between any portion of cable 80 and any portion of cable 20, even though the two are in use on the same patient at the same time.

Both cables 20 and 80, by means of their respective connectors 42 and 102, plug into a junction box which is depicted in FIGS. 8 through 14. This structure includes a printed circuit terminal board 110 and a molded plastic housing 112 (FIGS. 13 and 14) which encloses the terminal board. (In FIGS. 8 through 12, however, housing 112 is eliminated for clarity of illustration.) A multi-pin connector 114, which plugs directly into the ECG machine, is connected to terminal board 110 by a shielded, multi-line cable 116 which enters at the rear of housing 112 (see FIG. 13). Cable 16 is mechanically clamped to terminal board 110 by a U-shaped bracket 118 and suitable fasteners 120. Individual signal leads 122 emerge from cable 116 and are soldered to individual conductively plated through holes 124 formed in the board 110. A grounded shielding conductor 126 emerges from the outer wrapping of cable 116 and is soldered to another conductively plated through hole 128. Plated holes 124 are connected, by respective printed circuit leads 130 and 132 on the back side of board 110, to respective conductively plated through holes 134 and 136. Plated hole 128 is connected, by printed circuit leads 138 on the back side of the board 110, to conductively plated through holes 140. Grounded printed circuit leads 138 are grouped so as to surround the printed circuit signal leads 130 and 132 for shielding purposes, and also are interposed centrally to shield signal leads 130 from signal leads 132.

On the front side of board 110 are two rectangular sockets 142 and 144 into which printed circuit plug connectors 42 and 102 respectively of chest cable set 20 and arm-leg cable set 80 are longitudinally inserted. Within each of the sockets 142 and 144 are a plurality of spring contacts 146 (see FIGS. 11 and 12) which yieldingly mate with the connector contacts upon insertion of cable connector plugs 42 and 102. Respective pins 148 depend from contacts 146 into respective ones of holes 134, 136 and 140, and are soldered in place to establish electrical continuity from printed circuit leads 130, 132 and 138 to their respective contacts 146.

Rocker clamp mechanisms 150 and 152 serve to secure connector plugs 42 and 102 respectively in their inserted positions. Because of the fact that printed circuit leads 130, 132 and 138 are located on the back of terminal board 110, a convenient space is left clear on the front side of the terminal board for locating these clamp mechanisms. A pair of lugs 154 projects rearwardly from each socket 142 and 144. Respective pivot pins 156 are journaled within apertures formed in each pair of lugs 154. Each of two rocker clamps is formed with a pair of depending lugs 160 having apertures to receive the pivot pins 156, thus rockably mounting the clamps 158. Each rocker clamp is adapted to secure one of the cable connectors 42 or 102. Springs 164 are wrapped around respective pivot pins 156, and are torsionally compressed between terminal board 110 and their respective rocker clamps. As a result, rocker clamps 158 are each biased in the counter-clockwise direction (as viewed in FIGS. 11 and 12) about their respective pivot pins 156.

When either of the rocket clamps is in its biased position, a series of teeth 166 depending from rocker clamps 158 hold the spring contacts 146 against the inserted connector 42 or 102. These depending teeth ride in respective slots 168 formed in the top of each rectangular socket 142 and 144. In addition, fingers 170 depend from rocker clamps 158 and hook into apertures 171 which are formed in Mylar sheets 44 and 46 (FIG. 6) of connectors 42 and 102 to secure the connectors within sockets 142 and 144 respectively.

In order to insert or remove the connectors 42 or 102, the user simply exerts pressure against the rear end of rocker clamps 158, as indicated by arrow 172 in FIG. 12. The latter view shows the rocker clamp in its released position. Note that the releasing motion of the rocker clamp is limited when a projection 174 depending therefrom strikes terminal board 110.

Flexible housing 112 (FIGS. 13 and 14) surrounds the entire terminal board, along with all the electrical and mechanical components mounted thereon, and is formed with an entry opening 176 to admit connectors 42 and 102. Because of its flexibility, pressure on housing 112 at either of two marked areas 178 serves to depress the rear end of the nearby rocker clamp, thus releasing the clamp so that connector 42 or 102 can be inserted or released. Thus the clamp mechanisms hold the connectors securely, but are easy to release when necessary even though they are hidden inside housing 112.

It is now apparent that, by the single operation of plugging printed circuit connector 42 (FIGS. 1, 2 and 4–6) into the junction box of FIGS. 8–14, all six shielded chest leads are connected; and by the single additional operation of plugging printed circuit connector 102 (FIG. 7) into the junction box, all four shielded arm and leg leads are connected. This convenience, plus the lower risk of lead entanglement, make the cable sets of this invention easier and faster for the technician to use, as well as medically more reliable.

It is possible that other embodiments may also utilize the same novel features. For this reason, the description herein should be taken as merely exemplary, and not as limiting the scope of protection to be afforded this invention.

I claim:

1. A unitary medical cable set for electrical connection to a plurality of body locations, comprising:
   connector means for electrical connection to complementary connector means coupled to medical monitoring equipment, or the like, and having a plurality of electrical contacts;
   a plurality of electrical lead means each connected at one end to a respective one of said contacts; and
   support means secured to said connector means and supporting said plurality of lead means;
   said support means having a plurality of branches supporting respective ones of said lead means;
   said support means comprising a trunk portion secured to said connector means and supporting said plurality of lead means at a location proximate to said connector means, said trunk portion dividing to form said branches, at different spaced locations away from said connector means so as to prevent entanglement thereof, and said lead means diverging with said branches.

2. A medical cable set as in claim 1 further including attachment means electrically connected to each of said lead means and adapted to be secured mechanically and connected electrically to said respective body locations by means of respective disposable body electrode assemblies.

3. A medical cable set as in claim 2 further comprising at least one of said disposable body electrode assemblies; said disposable body electrode assembly including: conductive means, means for maintaining one side of said conductive means in contact with the body of a patient, and means including an adhesive layer for maintaining the opposite side of said conductive means in electrical contact with said attachment means.

4. A unitary medical cable set for electrical connection to a plurality of body locations, comprising:

connector means for electrical connection to complementary connector means coupled to medical monitoring equipment, or the like, and having a plurality of electrical contacts;

a plurality of electrical lead means each connected at one end to a respective one of said contacts; and support means secured to said connector means and supporting said plurality of lead means;

said support means having a plurality of branches supporting respective ones of said lead means;

said support means and said lead means comprising a flat structure including at least one flat sheet of insulating support material and a flat layer of flexible conductive lead material for each said lead means on a face of said support sheet, said support material being semi-flexible and said branches dividing at different spaced locations away from said connector means to prevent entanglement of said branches.

5. A medical cable set as in claim 4 wherein said connector means comprises an extension of said sheet of support material, and said contacts comprise respective flat conductors adhering to a surface of said sheet.

6. A medical cable set as in claim 4 further comprising another sheet of flexible insulating support material, and wherein each said flat layer of lead material is sandwiched between said two sheets of support material.

7. A medical cable set as in claim 6 wherein:

said connector means comprises a portion of a first one of said sheets of support material which extends beyond an edge of a second one of said sheets of support material whereby to expose a portion of an inner surface of said first sheet;

and said contacts comprise respective flat conductors adhering to said exposed surface;

said lead means emerging from the interior of said sandwich and extending beyond said edge of said second sheet to make electrical contact with respective ones of said contacts.

8. A medical cable set as in claim 6 further comprising at least one outer layer of flexible conductive shielding material on an outer surface of at least one of said support sheets.

9. A medical cable set as in claim 8 wherein:

said connector means comprises a portion of a first one of said sheets of support material extending beyond an edge of a second one of said sheets of support material whereby to expose a portion of an inner surface of said first sheet;

and said contacts comprise respective flat conductors adhering to said exposed surface;

a portion of said shielding layer extending beyond said edge of said second sheet to make electrical contact with one of said contacts.

10. A medical cable set as in claim 6 further comprising respective outer layers of flexible conductive shielding material on outer surfaces of each of said support sheets.

11. A medical cable set as in claim 10 wherein:

said connector means comprises a portion of a first one of said sheets of support material extending beyond an edge of a second one of said sheets of support material whereby to expose a portion of an inner surface of said first sheet;

and said contacts comprise respective flat conductors adhering to said exposed surface;

respective portions of said shielding layers extending beyond said edge of said second sheet to make electrical contact with respective ones of said contacts.

12. A medical cable set as in claim 11 wherein at least one of said shielding layers extends from said outer surface of said first sheet over an edge thereof and onto said inner surface thereof, and makes electrical contact with one of said contacts on said inner surface.

13. A medical cable set as in claim 4 further comprising a junction box for electrical connection to said connector means including a flat support sheet, contact means mounted on said support sheet and adapted to mate electrically with said contacts of said connector means, and spring-loaded clamping means arranged to clamp said connector means in place relative to said support sheet with said contacts of said connector means in electrically mated relationship with said contacts of said junction box.

14. A medical cable set as in claim 13 wherein said spring-loaded clamping means comprises rocker clamp means having opposite ends, a pivot intermediate said opposite ends, means engaging said intermediate pivot to mount said rocker clamp means upon said support sheet for rocking motion about said intermediate pivot, and spring means biasing said rocker clamp means so that a first one of said opposite ends clamps against said connector means, a second one of said opposite ends being spaced from said support sheet when said connector means is so clamped, and arranged so that depressing said second end toward said support sheet releases said connector means from said first end of said rocker clamp means.

15. A medical connector set as in claim 14 further comprising a flexible plastic housing closely surrounding said support sheet and said rocker clamp means, said housing having an opening to receive said connector means and an exterior marking indicating the location of said second end of said rocker clamp means whereby pressure exerted to flex said housing at said marked location pivots said rocker clamp means to release said connector means.

16. A medical cable assembly for making electrical contact with at least two groups of locations at different regions of a body; comprising:

at least two cables electrically coupled to a junction box;

each of said cables comprising connector means for electrical connection to complementary connector means coupled to medical monitoring equipment, or the like, and having a plurality of electrical contacts, a plurality of individual electrical lead means electrically connected at one end to respective ones of said contacts, and support means secured to said connector means and supporting said lead means, said support means being formed with a plurality of branches supporting respective ones of said lead means, respective attachment means at the end of each of said branches and electrically connected to its respective lead means remote from said connector means, said attachment means being adapted to be secured mechanically, and connected electrically, to respective different body locations;

said junction box being adapted to receive both of said connector means simultaneously, and comprising at least two different groups of contacts, the contacts of each group being adapted to mate electrically with respective contacts of a respective one of said connector means, respective spring-loaded clamp mechanisms including respective rocker clamp means adapted to clamp respective ones of said connector means with the electrical contacts thereof in electrically connected relationship with respective ones of said different groups of contacts, and releasable by pressure thereon at a selected location; and a flexible housing enclosing said clamp mechanisms and having at least one opening to receive both of said connector means simultaneously and respective exterior markings to indicate respective locations at which pressure may be exerted to flex said housing to release respective ones of said rocker clamp means.

17. A unitary medical cable set for electrical connection to a plurality of body locations, comprising:

connector means for electrical connection to complementary connector means coupled to medical monitoring equipment, or the like, and having a plurality of electrical contacts;

a plurality of electrical lead means each connected at one end to a respective one of said contacts; and support means secured to said connector means and supporting said plurality of lead means;

said support means having a plurality of branches supporting respective ones of said lead means;

said support means comprising a flat structure including at least one flat sheet of insulating support material supporting said lead means, said support material being semi-flexible and said branches dividing at different spaced locations away from said connector means to prevent entanglement of said branches.

18. A unitary flat medical cable set for electrical connection to a plurality of body locations, comprising:

connector means for electrical connection to complementary connector means coupled to medical monitoring equipment, or the like, and having a plurality of electrical contacts;

flat support means comprising a trunk portion secured to said connector means;

a plurality of flat branches integral with and supported by said trunk portion, said branches dividing from said trunk portion at different spaced locations away from said connector means;

said trunk portion and said branches comprising a unitary flat flexible structure including at least one flat sheet of flexible insulating support material; and a plurality of lead means each connected at one end to a respective one of said contacts and extending along said trunk portion and along a respective one of said branches, said lead means each comprising a flat layer of flexible conductive lead material on a face of said support sheet.

* * * * *